(12) United States Patent
Landis et al.

(10) Patent No.: US 8,814,838 B2
(45) Date of Patent: Aug. 26, 2014

(54) RESPIRATORY SECRETION RETENTION DEVICE, SYSTEM AND METHOD

(75) Inventors: Robert M. Landis, Mountainside, NJ (US); Charles A. Lewis, Carrabelle, FL (US); Angelo Caruso, Boca Raton, FL (US); Bruce Sher, Lighthouse Point, FL (US); Louis Javier Collazo, Pompano Beach, FL (US); Sanjay Chandran, Boca Raton, FL (US)

(73) Assignee: Mergenat Medical, Inc., Coconut Creek, FL (US)

( * ) Notice: Subject to any disclaimer, the term of this patent is extended or adjusted under 35 U.S.C. 154(b) by 336 days.

(21) Appl. No.: 12/431,069

(22) Filed: Apr. 28, 2009

(65) Prior Publication Data

US 2010/0089399 A1   Apr. 15, 2010

Related U.S. Application Data

(60) Provisional application No. 61/104,597, filed on Oct. 10, 2008.

(51) Int. Cl.
*A61M 1/00* (2006.01)
*A62B 7/10* (2006.01)

(52) U.S. Cl.
USPC .................... 604/317; 128/205.2; 128/205.27

(58) Field of Classification Search
USPC ............ 128/205.12, 205.27, 205.29, 206.22; 604/317, 319
See application file for complete search history.

(56) References Cited

U.S. PATENT DOCUMENTS

| RE39,508 E | * | 3/2007 | Parker ...................... 128/200.26 |
| 2002/0108614 A1 | * | 8/2002 | Schultz .................... 128/207.14 |

* cited by examiner

*Primary Examiner* — Melanie Hand
(74) *Attorney, Agent, or Firm* — Adam C. Underwood

(57) ABSTRACT

A novel and non-obvious apparatus, system, and method for managing respiratory secretions and fluids in sections of artificial airways. In an embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and at least one element configured to provide for repositioning at least a portion of the housing with respect to the artificial airway. In an aspect of this embodiment, the at least a portion of the housing can be repositioned with respect to the artificial airway without opening the artificial airway to the atmosphere.

25 Claims, 17 Drawing Sheets

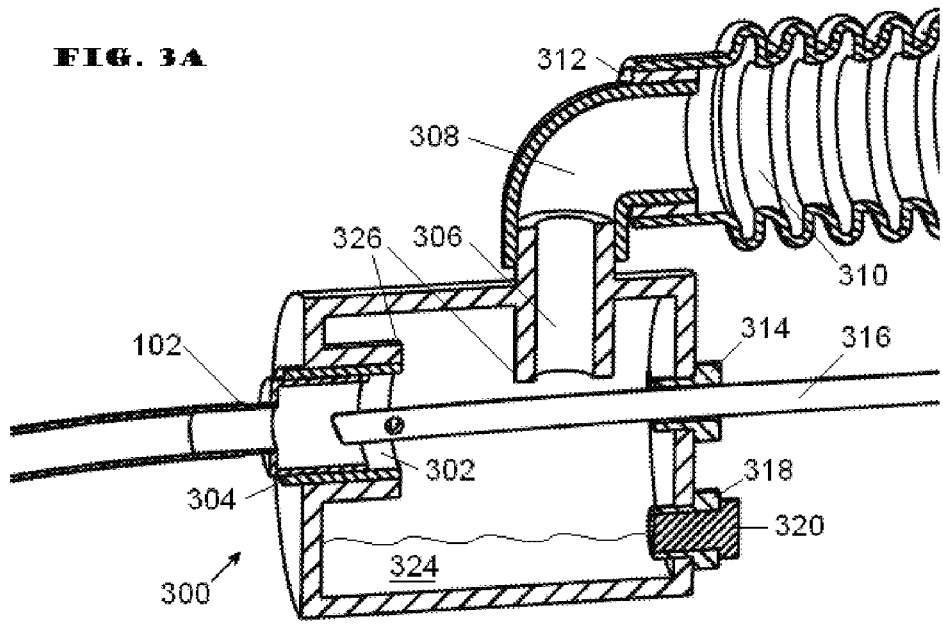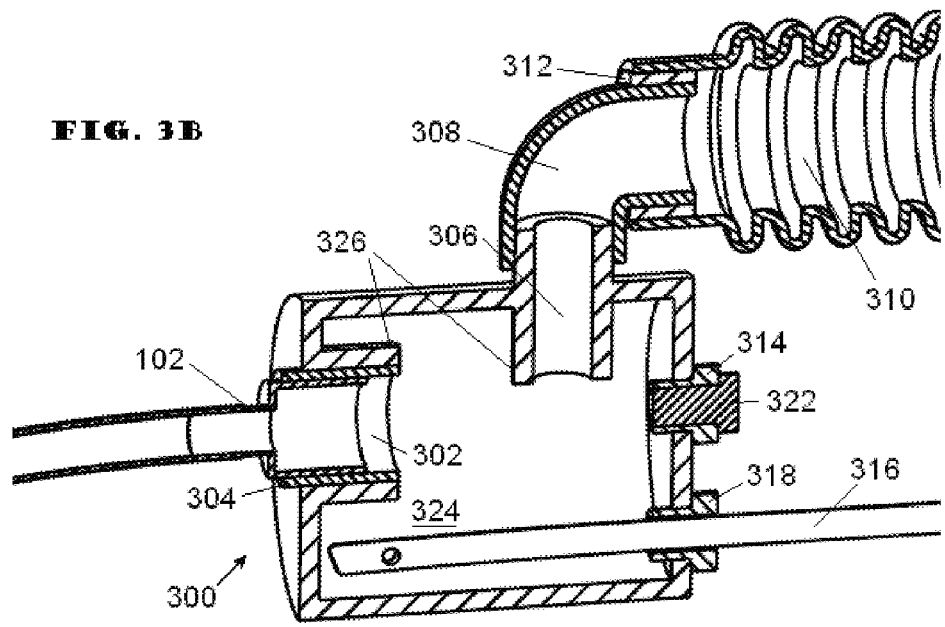

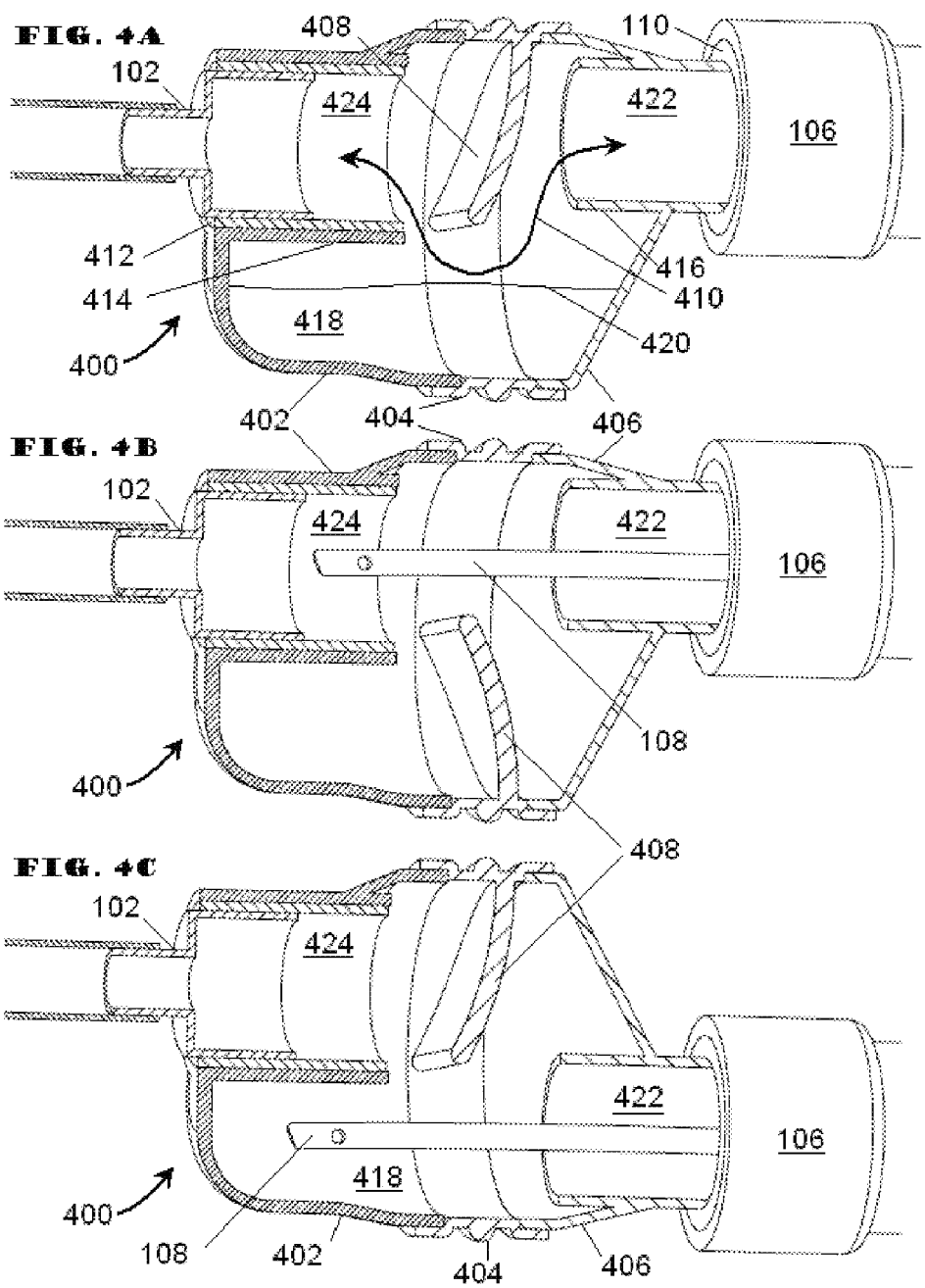

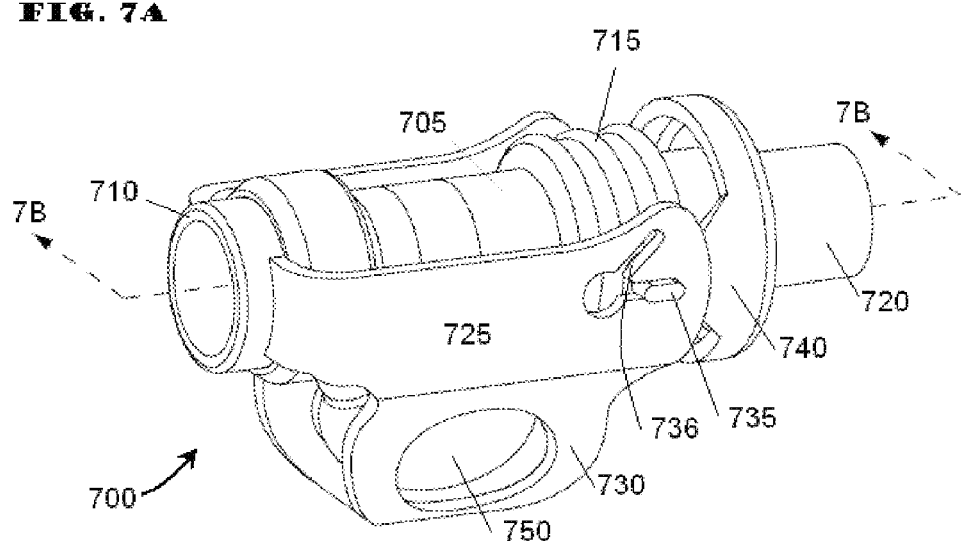
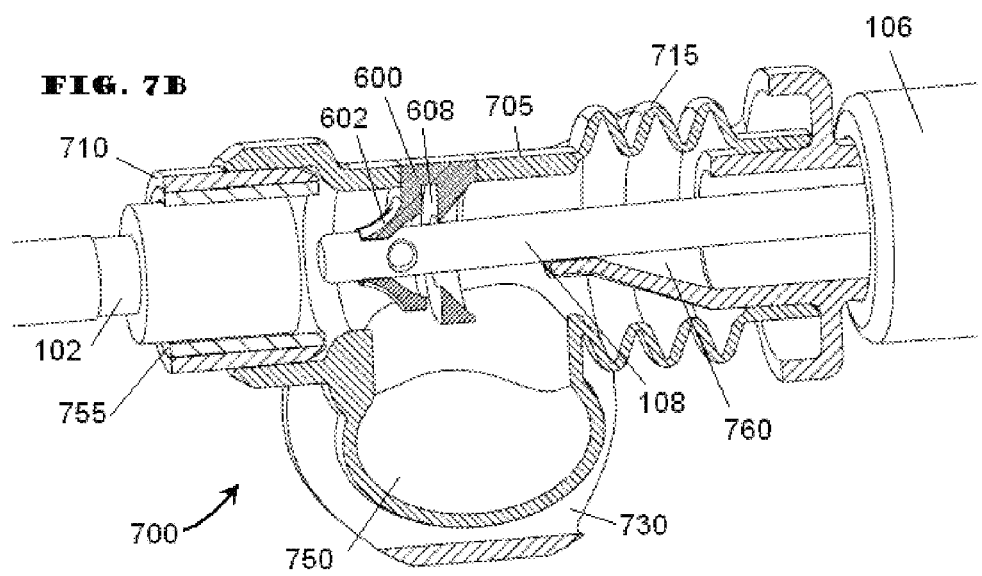

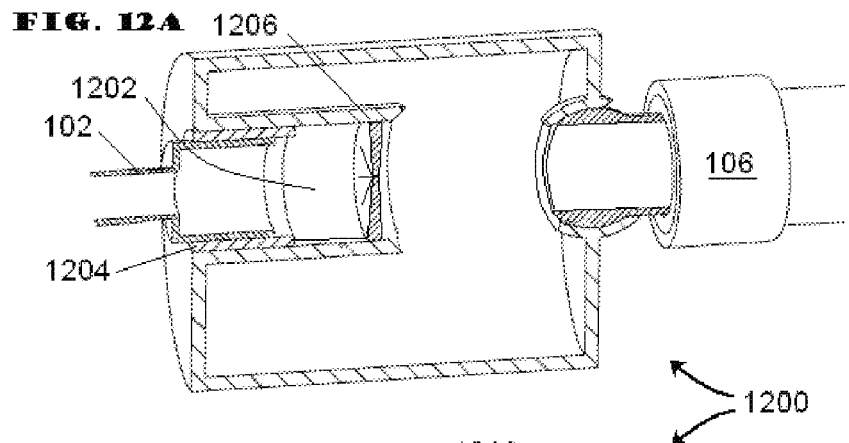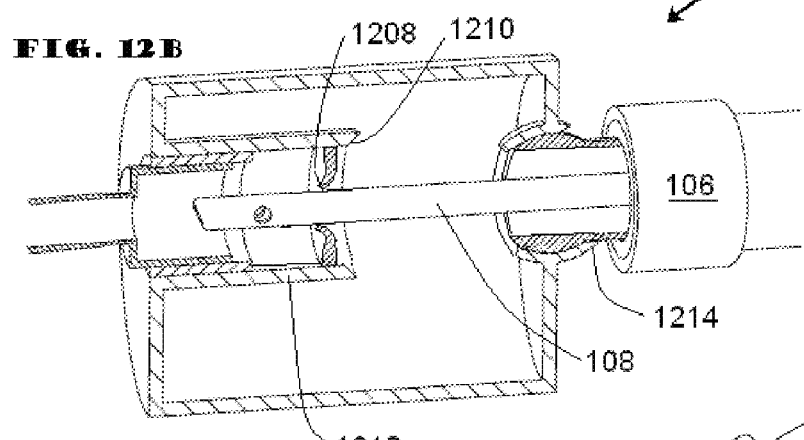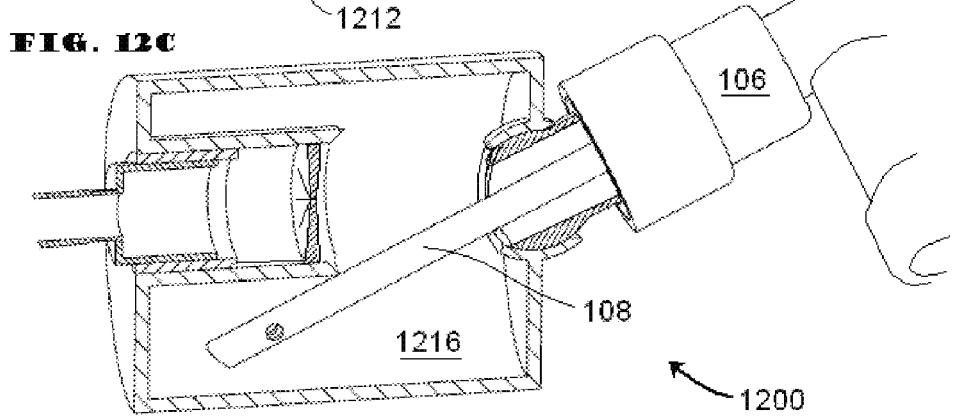

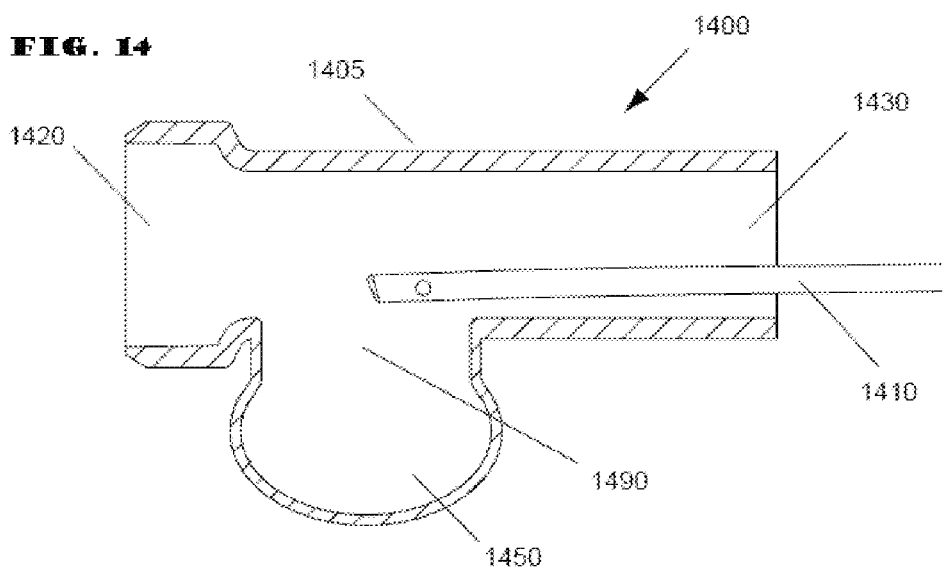

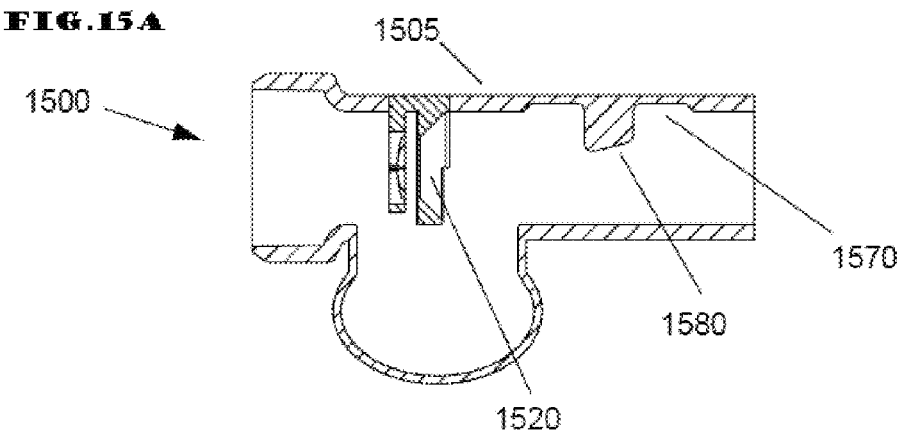
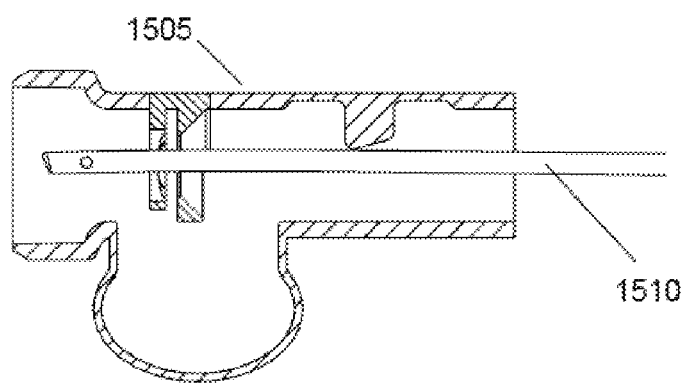
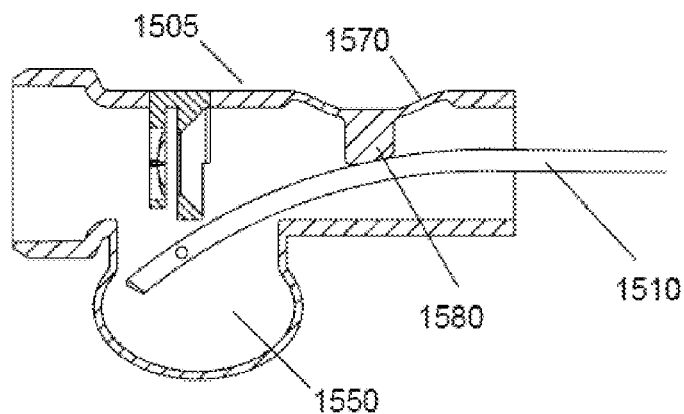

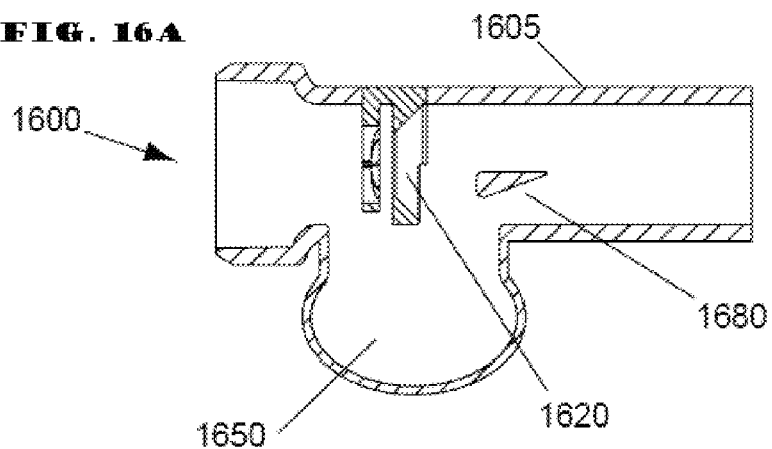
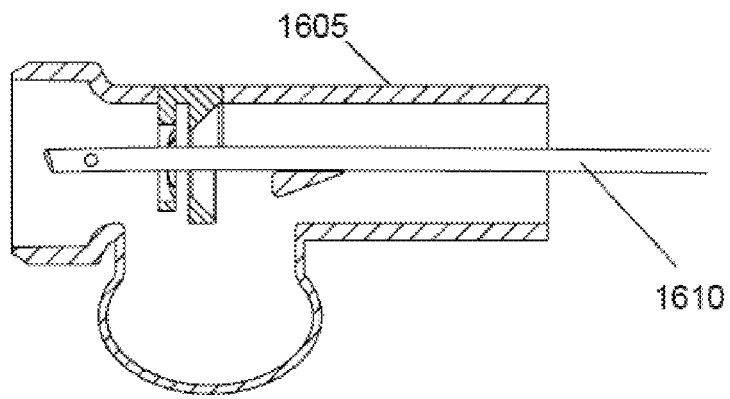
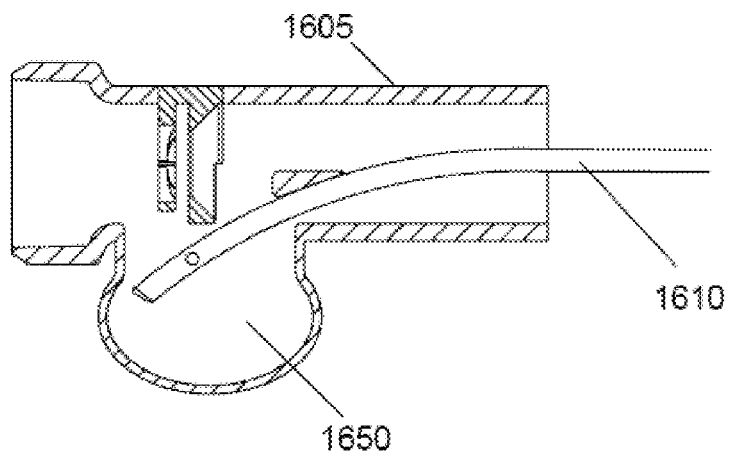

RESPIRATORY SECRETION RETENTION DEVICE, SYSTEM AND METHOD

RELATED APPLICATIONS

This application claims benefit and priority of U.S. Provisional Patent Application Ser. No. 61/104,597 filed Oct. 10, 2008, the entire contents of which are incorporated herein by reference thereto.

BACKGROUND OF THE INVENTION

1. Statement of the Technical Field

The present invention relates to artificial airways and more particularly to an airway device for controlling respiratory secretions in artificial airways, and associated devices such as respiratory gas delivery devices.

2. Discussion of the Related Art

The use of artificial airways is a common method of maintaining an open airway for patients who require some type of respiratory assistance. Artificial airways come in a variety of options depending on the patient and level of respiratory intervention required. Large numbers of artificial airways have three common features. First, the artificial airway will be a flexible tube that extends into the patient's trachea. Second, most artificial airways will have an inflatable cuff near the distal end of the tube. The inflatable cuff can be used to make an airtight seal, e.g., for nasal tracheal, oral tracheal and tracheostomy tubes where the entire breath of the patient is directed through the tube. Third, the standard artificial airway has a 15 mm fitting on the external opening of the tube to which respiratory instruments can be attached compliant with the ISO 5356; Anesthetic and Respiratory Equipment—Conical Connectors standard.

One of the common issues with having the patient breathe through these artificial airways is that respiratory secretions, which would normally enter the pharynx and get swallowed, expectorated or coughed out through the mouth, are forced to egress through the lumen of the artificial airway. The presence of the tube, being a foreign object in the airway can also stimulate respiratory secretions.

Keeping the tube and airway clear of secretions is a procedure performed by clinicians, which requires training and vigilance. Depending on the condition of the patient, the frequency of clearing the airway with a suction catheter varies greatly. When secretions accumulate in the tube there is added resistance to breathing and when the patient is strong enough, a forceful exhalation sends the secretions out through the tube and into the room or into any device attached to the tube.

Some fluid trap devices for use between an ET tube and a ventilator circuit have a fill volume substantially independent of orientation of the trap within the fluid circuit. Such fluid trap devices are disadvantageous as they impose unnecessary and excessive dead-space (e.g., exhaled air that is re-breathed) to achieve the independent orientation.

Typically, when an instrument is detached from a tube adapter the patient coughs and respiratory secretions and fluids are sprayed into the room. In addition, it is common for a patient on a ventilator to have secretions accumulate inside the endotracheal (ET) Tube with no place to go but up the tube, down the tube or into what ever breathing instrument is attached to the ET Tube.

In the last decade, the use of "closed suction" devices has become a standard at many medical facilities. A closed suction device allows for access to the airway with a suction catheter without detaching or removing the treatment device from the artificial airway. Closed suction systems add additional support to clinicians by greatly reducing the time and effort necessary for clearing the airway. A closed suction device for example, can allow a catheter to advance into the artificial airway for suctioning and then withdrawn into a protective sheath where it is protected from contamination when the catheter is not in use. The closed suction catheter may be used multiple times without opening the device to the atmosphere, and is usually used for one to several days. A closed suction system allows access to the ventilator breathing circuit connected with the patient to remain "closed" as opposed to methods that require it to be "opened" to the atmosphere for access. Closed suction also reduces risk of microbial contamination of the artificial airway during suctioning thereby protecting the patient's airway from infection. In numerous medical institutions, the infection control departments have made the use of closed suction a standard of practice by requiring that all intubated patients in the intensive care unit (ICU) have a closed suction system installed.

Most clinicians find that there are a significant number of instances when it is necessary to detach a respiratory instrument or "open the circuit" and during these occasions additional protection is most welcomed.

There are three main problems with secretions in the breathing tube. First, when the breathing tube is disconnected, secretions can be sprayed into the room if the patient coughs. Second, clearance of the artificial airway may be delayed resulting in compromised breathing. Third, when secretions are forced out into the attached breathing instruments, these secretions can foul the attached instruments, such as a heat and moisture exchange (HME) device, and the like.

SUMMARY OF THE INVENTION

Embodiments of the present invention address deficiencies of the art in respect to artificial airways and respiratory secretions management and provide a novel and non-obvious apparatus, system, and method for managing respiratory secretions and fluids in a section of artificial airways. In an embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and at least one element configured to provide for repositioning at least a portion of the housing with respect to the artificial airway. In an aspect of this embodiment, the at least a portion of the housing can be repositioned with respect to the artificial airway without opening the artificial airway to the atmosphere.

In another embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and at least one flow diverter positioned in the expiratory flow passageway of the housing. In an aspect of this embodiment, the at least one flow diverter positioned in the expiratory flow passageway of the housing includes an aperture that defines an instrument passage.

In yet another embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and a medical instrument port coupled within the housing and a medical instrument configured to advance into and through the housing of the respiratory secretion retention device without opening the respiratory secretion retention device to the atmosphere. In an aspect of this embodiment, at least a portion of the chamber is configured to provide for repositioning of the chamber to remove the retained secretions from within the device.

In still another embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and an expiratory port of the housing, wherein the expiratory port is substantially aligned to a gas delivery port of the housing. In an aspect of this embodiment, the housing is configured to provide for repositioning of the gas delivery port with respect to the expiratory port.

In still another embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and an expiratory port of the housing, wherein the expiratory port is substantially aligned to a gas delivery port of the housing. In an aspect of this embodiment, the housing is configured to provide for repositioning of the gas delivery port with respect to the expiratory port.

In still yet another embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and a clip coupled to the reservoir and configured to limit the volume of the reservoir to the area of the reservoir above the clip. In an aspect of this embodiment, the reservoir has an access port for the removal of the retained secretions.

In an embodiment of the invention, the airway conduit can include a section of the conduit in which the cross-sectional area of the conduit widens, and thus slows the flow of gases and respiratory secretions, thereby allowing material with greater mass to separate out from the gas flow.

In an embodiment of the invention, the direction of the gas flow path is indirect. An indirect path can cause respiratory secretions, which have more mass than the gas to separate from the gas flow. In a related embodiment, an indirect path can cause respiratory secretions, which have more mass than the gas, to impact surfaces within the device and thus separate from the gas flow.

In an embodiment of the invention, a partial barrier or gas flow diverter may be configured into the gas flow path within the airway conduit so that respiratory secretions which have more mass than the gas are likely to impact the surface of the barrier or diverter and are separated from the gas flow. The diverter can include a hydrophobic surface to decrease the adherence of the respiratory secretions to the partial barrier or diverter.

In an embodiment of the invention, one or more areas can be configured to retain respiratory secretions. In an embodiment of the invention a porous or absorbent media may be used to aid in the retention of respiratory secretions.

In an embodiment of the invention the airway conduit can be configured to limit the egress of respiratory secretions from the device.

In an embodiment of the invention the airway conduit can be configured to allow for removal of retained respiratory secretions from the device without disconnecting or opening the breathing circuit to atmosphere.

In an embodiment of the invention, the airway conduit can be configured to link to a suction device which allows automatic, intermittent or continuous removal of respiratory secretions which may collect within the device.

In an embodiment of the invention, the airway conduit can be configured to link to a closed suction device that allows suctioning of the artificial airway or the lower respiratory system through the airway conduit.

In an embodiment of the invention, a partial barrier or diverter disposed within the housing can be configured so that a suction catheter may pass through the barrier or diverter.

In an embodiment of the invention, a partial barrier or diverter may be configured so that a suction catheter can pass through the diverter or a portion of the diverter or the diverter can flex to move out of the way of the suction catheter.

In an embodiment of the invention the airway conduit can include a feature to help guide a suction catheter.

In an embodiment of the invention, the airway conduit housing can be configured to alter its conformation to allow suction through the conduit in one conformational position, and suction of the secretions retained within the conduit in another conformational position.

In an embodiment of the invention, the airway conduit may be configured with a connector for the respiratory gas delivery conduit near the patient side of the RSR device. The connector for the respiratory gas delivery conduit can be in the form of a Tee or a Wye. This configuration can decrease dead air space. In this configuration, expiratory gas flow is designed to go through the RSR device while inspiratory flow enters from the patient end of the device.

In an embodiment of the invention, the RSR device can be configured so that a reservoir, utilizing gravity, collects the respiratory secretions into a certain area. In an embodiment of the invention, the RSR device may be configured with a swivel fitting at one or more connector fittings, to allow the RSR device to be positioned so that the reservoir of the device may be placed in a dependent orientation, utilizing gravity to direct the secretions into a reservoir area. In an embodiment, the connector to the artificial airway tube may be a 15 mm female fitting. In other embodiments, the fitting at the patient end of the device may couple directly with the artificial airway tube. In an embodiment of the invention, the RSR may be configured with an integrated closed suction feature. In an embodiment of the invention, the RSR may be configured with integrated heat and moisture exchange capabilities.

Additional aspects of the invention will be set forth in part in the description which follows, and in part will be obvious from the description, or may be learned by practice of the invention. The aspects of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute part of this specification, illustrate embodiments of the invention and together with the description, serve to explain the principles of the invention. The embodiments illustrated herein are presently preferred, it being understood, however, that the invention is not limited to the precise arrangements and instrumentalities shown, herein:

FIGS. 3A and 3B are cross-sectional schematic illustrations of yet another RSR device according to a certain embodiment of the present invention;

FIG. 4 shows cross-sectional schematic illustrations of yet another RSR device according to a certain embodiment of the present invention;

FIG. 7 shows schematic illustrations of yet another RSR device according to a certain embodiment of the present invention;

FIG. 12 shows cross-sectional schematic illustrations of variations of the RSR device shown according to a certain embodiment of the present invention;

FIG. 14 shows a cross-sectional schematic illustration of the RSR device according to a certain embodiment of the present invention;

FIG. 15 shows cross-sectional schematic illustrations of variations of the RSR device shown according to a certain embodiment of the present invention;

FIG. 16 shows cross-sectional schematic illustrations of variations of the RSR device shown according to a certain embodiment of the present invention; and, FIG. 17 shows front schematic illustrations of variations of the RSR device shown according to a certain embodiment of the present invention.

DETAILED DESCRIPTION OF THE INVENTION

Figure 1A:
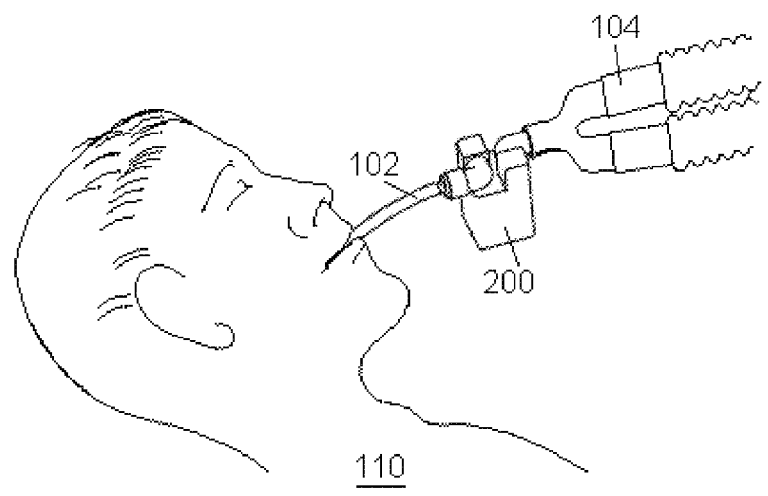
FIGS. 1A and 1B are schematic illustrations of the placement of an RSR device showing its attachment to an artificial airway in an intubated patient, where the RSR device is also connected to a ventilator circuit in FIG. 1A and wherein an RSR device is connected to a closed suction catheter in FIG. 1B.

During the exhalation phase of respiration fluid is expelled from the lower respiratory tract. Most of the fluid are in the form of gases, but liquid and particulate matter are also expelled. The RSR acts to separate the "respiratory secretions" and "airway fluids" from the respiratory gasses. For purposes of this disclosure, "respiratory secretions" and "airway fluids" may include sputum, mucus, mucus plugs, and/or other all other nongaseous matter which may be conveyed out of the lower respiratory tract and the like.

Embodiments of the present invention address deficiencies of the art in respect to artificial airways and respiratory secretion management, and provide a novel and non-obvious apparatus, system, and method for managing respiratory secretions and fluids in artificial airways. In an embodiment of the invention, a Respiratory Secretion Retention (RSR) device for connecting to an artificial airway can be provided. In an embodiment of the invention, a respiratory secretion retention (RSR) device configured to connect to an artificial airway can be provided. The respiratory secretion retention (RSR) device can include a housing that defines a passageway for the flow of respiratory gases, a chamber that is defined by the housing, where a portion of the chamber is configured to retain exhaled respiratory particulate and liquid, and at least one element configured to provide for repositioning at least a portion of the housing with respect to the artificial airway. In an aspect of this embodiment, the at least a portion of the housing can be repositioned with respect to the artificial airway without opening the artificial airway to the atmosphere.

In another embodiment of the invention, a respiratory secretion retention (RSR) device can include a housing that defines a passageway for the flow of respiratory gases, a chamber that is defined by the housing, where a portion of the chamber is configured to retain exhaled respiratory particulate and liquid, and at least one flow diverter positioned in the expiratory flow passageway of the housing. In an aspect of this embodiment, the at least one flow diverter positioned in the expiratory flow passageway of the housing includes an aperture that defines an instrument passage. In yet another embodiment of the invention, a respiratory secretion retention (RSR) device can include a housing that defines a passageway for the flow of respiratory gases, a chamber that is defined by the housing, where a portion of the chamber is configured to retain exhaled respiratory particulate and liquid, and a medical instrument port coupled within the housing and a medical instrument configured to advance into and through the housing of the respiratory secretion retention device without opening the respiratory secretion retention device to the atmosphere. In an aspect of this embodiment, at least a portion of the chamber is configured to provide for repositioning of the chamber to remove the retained secretions from within the device.

In illustration, FIG. 1A is a schematic illustration of an RSR device 200 attached to an endotracheal (ET) tube 102 in an intubated a patient 110. The RSR device 200 also can be attached to a ventilator circuit 104. The patient 110 is shown at an approximately 45-degree angle from level as this position as recommended by the CDC for prevention of ventilator associated pneumonia. This illustration shows the relationship of the RSR device 200 used in association with a ventilator circuit 104. The device can also be used in association other ventilation tubes such as with a tracheostomy tubes, or nasotracheal tubes. RSR 200 can be used alone with an artificial airway 102 without a ventilator 104, such as in a spontaneously breathing patient.

Figure 1B:
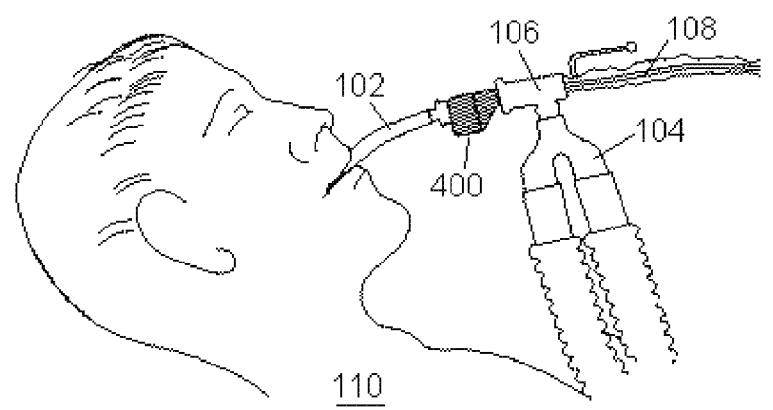

FIG. 1B illustrates a closed suction device 106 that can be connected between the RSR device 400 and the ventilator circuit 104. Certain embodiments of the present invention allow for the use of closed suction, and allow a suction catheter 108 of the closed suction device 106 to pass through RSR device 400 and into and through the patient's artificial airway in accordance with an embodiment of the present invention.

Figure 2A:
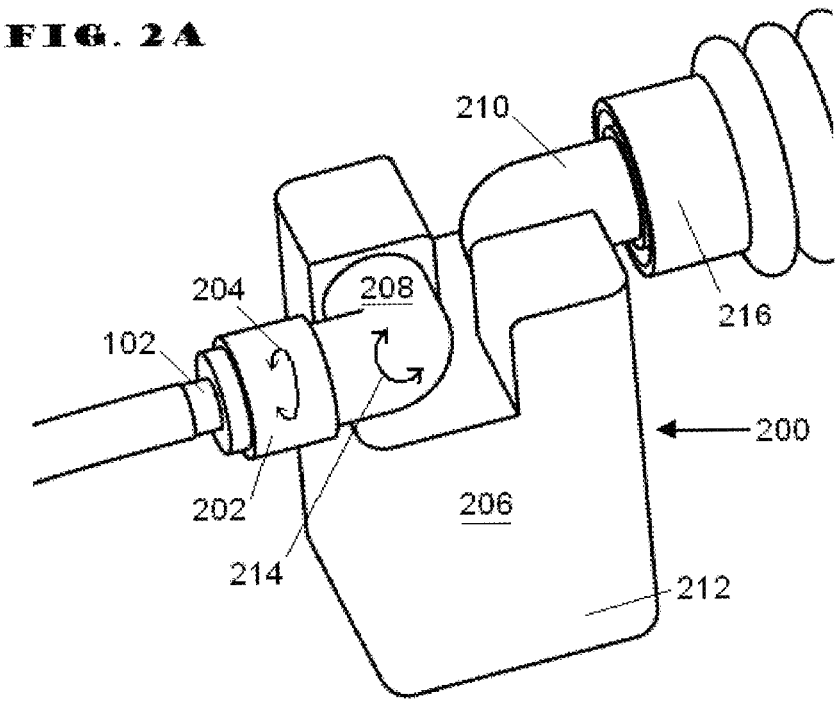
FIGS. 2A and 2B are schematic illustrations of an RSR device according to a certain embodiment of the present invention.

FIG. 2A is a schematic illustration of an RSR device 200 showing detail of its attachment to the endotracheal tube 102 and to the ventilator circuit. The RSR device can be applied so that gravity pulls secretions into a dependent area of the housing configured to retain the respiratory secretions. In embodiments, swivels can be added to the RSR to articulate the device in order to adjust it into a dependent position with respect to the collection of respiratory secretions, so that gravity pulls the secretions into a dependent area of the housing configured to retain the respiratory secretions.

The typically male fitting of the artificial airway 102 (as illustrated in FIG. 2A) fits into the typically female 15 mm fitting 202 which in preferred embodiments of this invention is configured as a swivel fitting. The rotation of this fitting is indicated by arrow 204. Fitting 202 can be connected to the RSR main body 206 with tube 208. Tube 208 can be straight or tube 208 may be angled and/or rotatable. A second tube 210 can be located on the ventilator side of the RSR device 200. Tube 210 can be straight or tube 210 can be angled and rotatable. In embodiments, tube 208 and tube 210 can swivel to allow the reservoir area of main body 206 to be placed in a dependent orientation while allowing the patient to be placed in a variety of positions. RSR device 200 can be designed to be used where its reservoir area 212 is placed below the artificial airway 102. Arrows 214 show the possible articulation of the angled and rotatable tubes in one embodiment in relation to the main body 206. Tube 210 is shown connected to a female ventilator connection 216 which also can contain a swivel. Thus, the main body 206 of the RSR 200 may move in two axes and the reservoir area 212 can be oriented in a dependent position with respect to gravity.

Figure 2B:
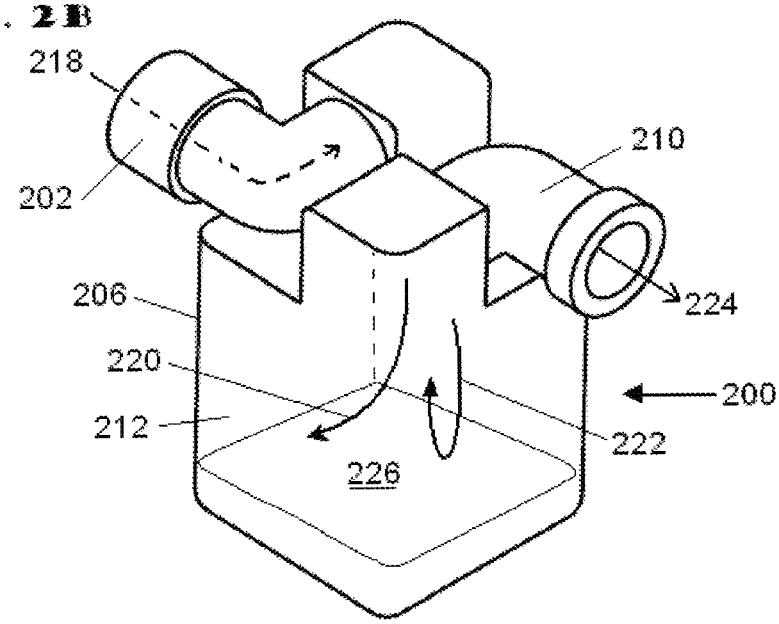

FIG. 2B further illustrates the air flow path of RSR device 200, illustrating its function. When the patient exhales, the flow enters connector 202 through the artificial airway into the RSR device 200 as shown by arrow 218. The momentum of the heavier fluids (respiratory secretions) causes them to both impact the interior surfaces of the RSR device and to fall out of the gas flow when the flow channel widens in the RSR and gas flow slows. This occurs in the RSR main body 206, and flow is indicated by arrows 220 and 222. Outflow of expiratory gasses is shown by arrows 224. On inhalation the gases reverse the flow direction in this embodiment of the invention. A fluid level of trapped respiratory secretions 226 is shown.

FIG. 2B shows RSR device 200 according to an embodiment of this invention which allows for control of the orientation of the reservoir area for collection of respiratory secretions. In order to retain the secretions, it is important that these secretions are unlikely to exit the reservoir area of the main housing 206 and unlikely to drain back into the patient's airway. Thus the ability to position the reservoir in a dependent orientation is an important feature of this invention. As the patient may be moved, it is advantageous to have a device which allows the orientation of the reservoir to move without disconnecting the device which would open the airway and allow possible contamination of the airway. A sputum trap that is insensitive to orientation has the disadvantage of an increased dead air space, and thus creates an added burden for $CO_2$ removal during respiration.

FIG. 3A illustrates others embodiment of an RSR device according to an embodiment of the present invention. In FIG. 3A, RSR device 300 is shown as a cross-sectional schematic. Patient airway port 302 allows for connection to artificial airway 102 typically with a 15 mm male connector via swivel connector 304. Ventilation source port 306 is shown with a 90 degree angled arm 308, which can rotate according to one configuration of the present invention, and is shown linked to a corrugated tubing 310 via swivel fitting 312. Ventilation source port 306 also can have a swivel.

Suction access ports 314 and 318 are plugged when not in use, as shown by plug 320 which seals port 318 in FIG. 3A, and plug 322 sealing port 314 in FIG. 3B. Access port 314 allows for the introduction of a suction catheter 316 that may suction the artificial airway 102 as illustrated in FIG. 3A, or may be used for the introduction of another instrument such as a bronchoalveolar lavage tube. Access port 318 allows for introduction of a suction catheter 316 as shown in FIG. 3B or for the introduction of another instrument such as a needle for example for removal of collected respiratory secretions which may collect in the reservoir area 324. In a variation of this device (such as described in FIG. 11A) a fitting for closed suction may be attached. Swivel connectors 304 and 312 allow for control of orientation of the RSR device 300.

FIGS. 3A and 3B also illustrate spill guards 326, which extend from the inner wall of the RSR device 300, and help prevent unintended emptying of the liquid contents of the reservoir back into the artificial airway or into the gas delivery limb in the case of movement or change in position.

FIGS. 4A, 4B and 4C show cross-sectional schematic illustrations of another RSR device according to a certain embodiment of this invention, and each illustration shows a different conformational position of RSR device 400.

FIG. 4A is a cross sectional view of an RSR device 400 having a 3 sections which can rotate in reference to each other. RSR device 400 includes a patient interface section 402, a middle section 404 with a diverter 408, and a ventilation source section 406. FIG. 4A shows RSR sections 402, 404 and 406 in their typical use conformational orientation. RSR device 400 changes its conformation by changing the rotation positions of the sections 402, 404 and 406. RSR device 400 is configured so that the interior walls form a gas flow chamber, and a reservoir area for retained respiratory secretions.

The diverter 408 is configured to redirect the gas flow and to separate respiratory secretions that may be expelled during exhalation. Diverter 408 is disposed substantially perpendicular to the inflow path of the artificial airway 102. The diverter acts as an obstacle in the expiratory fluid pathway. As the respiratory secretions have more mass, and thus more momentum, they do not flow around the tortuous flow path created by the diverter as easily as the lighter gases in the exhalation, and are more likely to impact the surface of the diverter and the interior of the housing, to loose velocity and thus be separated from the gas flow. The fluid flow through the RSR devices also slows as a result of the widening of the cross-section of the flow path within the housing where the flow chamber is formed. This also decreases the momentum and acts to separate the respiratory secretions from the gases in the exhalation, and helps to retain these secretions within the chamber. A simplified gas flow path for the RSR device 400 when in the typical use position is illustrated by arrow 410.

The orientation of the reservoir area 418 helps retain the heavier fluids in the body of the RSR device 400. A fluid line 420 is shown to help illustrate fluid in the reservoir area. The dependent area 418 forms a reservoir for respiratory secretions. Swivel 412 in artificial airway port 424 allows for orientation of the RSR in relation to the artificial airway 102. An RSR device may also be configured with a swivel on the ventilator source section; however a swivel is not usually required on the ventilation source end of the RSR device 400 where it attaches to ventilation port 424 for use with a closed suction device 106, as the closed suction device typically contains its own swivel 110.

Also illustrated are spill guards 414 and 416, which show that the inlets to the connection ports from the inner housing of the RSR are configured to prevent the efflux of the retained secretions. Spill guards 414 and 416 advantageously prevent respiratory secretions and liquids from leaving the RSR device 400 and entering the HME, the breathing circuit and/or the artificial airway. Accordingly, the spill guards 414 and 416 help prevent egress of collected airway fluids into respiratory instruments when the patient turns or moves for example, and makes the device less susceptible to egress of retained fluids with movement of the patient.

In FIG. 4B, middle section 404 is shown rotated 180 degrees in relation to the typical use conformational position of sections 402 and 406. This allows diverter 408 to move out of a direct path between the ventilation source port 422 and the artificial airway port 424. As further illustrated in FIG. 4B, this conformational positioning allows the suction catheter 108 of the closed suction device 106 attached to the ventilation source port 422 to be advanced through the body of RSR 400 and into the artificial airway 102 for suctioning. After suctioning of the artificial airway, catheter 108 can be withdrawn into the closed suction device 106 and the RSR device 400 can be returned to it typical use conformational alignment. Other instruments such as a bronchial alveolar lavage device may also be passed through the RSR device in a similar manner.

In FIG. 4C, the ventilation source section 406 of RSR device 400 is shown rotated 180 degrees with relation to the typical use position of sections 402 and 404. This allows the suction catheter 108 of the closed suction device 106 to be advanced into the reservoir area 418 of the body of RSR device 400 for suctioning and evacuation of retained fluids. After clearing the retained respiratory secretions from the reservoir area, catheter 108 can be withdrawn into the closed suction device 106 and the RSR device 400 can be returned to it typical use position conformational alignment.

Figure 5A:
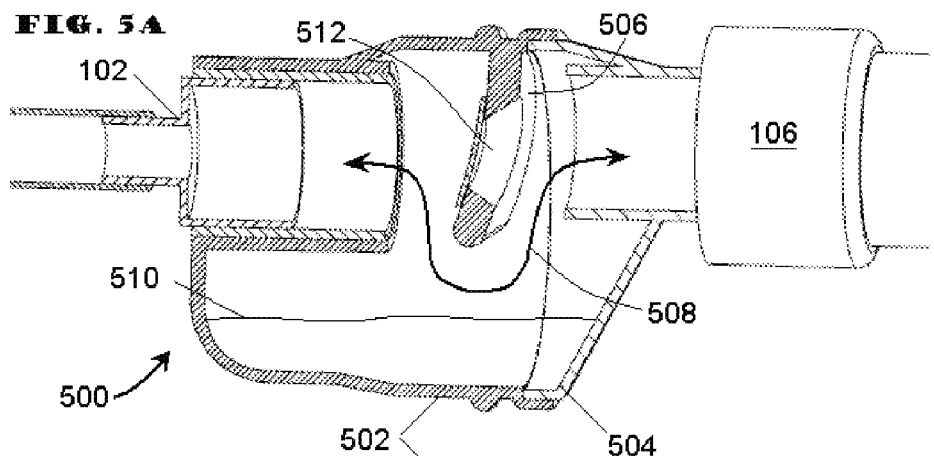
FIG. 5 shows schematic illustrations of yet another RSR device according to a certain embodiment of the present invention.

FIG. 5A is a schematic illustration of another RSR device according to a certain embodiment of this invention that illustrates a diverter 506 placed in the path of the gas flow, which allows for the passage of a suction catheter through the diverter 506. The arrow 508 in FIG. 5A shows the flow pattern of respiratory gasses through the chamber formed by the housing of RSR device 500 when it is in its typical conformational position for use for retaining respiratory secretions from exhaled respiration. Respiratory secretions are indicated by fluid line 510 where the housing of RSR device 500 acts as a reservoir area. The housing of device 500 has two main chamber sections. The patient interface section 502 is on the artificial airway side, and the ventilation source section 504 is on the ventilation source side. These two sections may have a circular cross section and are configured so that they are rotatably connected to one another.

Figure 5B:
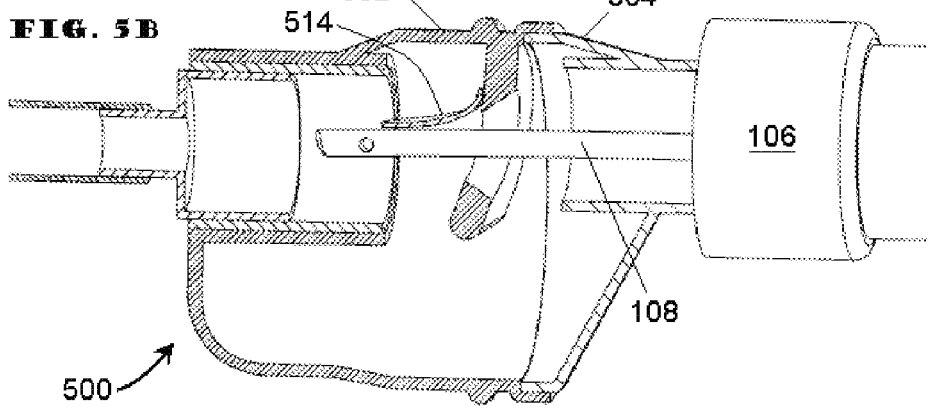

In FIG. 5A section 502 is shown with a respiratory gas diverter 506 attached to a portion of the inner wall of device 500. Diverter 506 features an orifice 512. Orifice 512 is shown with a funnel shape which can act as an instrument guide for helping pass an instrument, such as suction catheter (108) through this orifice as shown in FIG. 5B. A valve 514, shown here as a flap valve, closes orifice 512 and limits expiratory flow from passing through the orifice 512, but allows the passage of an instrument as shown in FIG. 5B. In alternative embodiments, a valve may not be required as orifice 512 may be sized small enough such that it limits the passing of expiratory flows and secretions FIG. 5B illustrates RSR device 500 during the use of an instrument intended to enter the artificial airway. Valve 514 is shown in the open position, held open by suction catheter instrument 108, extending from a closed suction device 106. Other instruments such as a bronchial alveolar lavage catheter may also be used.

Figure 5C:
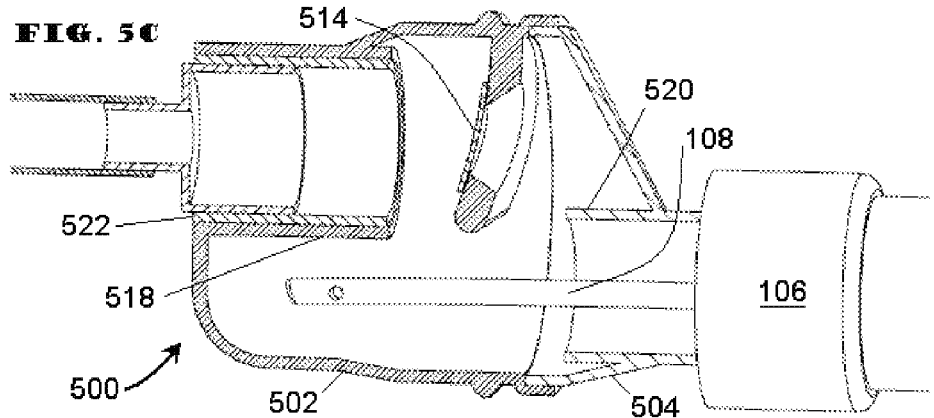

FIG. 5C illustrates RSR device 500 in a second conformational position. The two main chamber sections 502 and 504 are shown rotated 180 degrees in relationship to each other. This conformational arrangement allows the suction catheter 108 to be used to remove retained fluids and other respiratory secretions from the RSR device 500 which have collected in the reservoir area.

FIG. 5B further illustrates spill guards 518 and 520, which can be included in RSR devices according to certain configurations of this invention. The spill guards 518, 520 advantageously prevent respiratory secretions and liquids from leaving the RSR device 500 and entering the HME, breathing circuit, or the patient's artificial airway. Accordingly, the spill guards 518 and 520 help prevent egress of collected airway fluids into respiratory instruments or into the artificial airway, for example when the patient turns or moves. FIG. 5C also marks a swivel 522 in the artificial airway port connector.

Figure 6A:
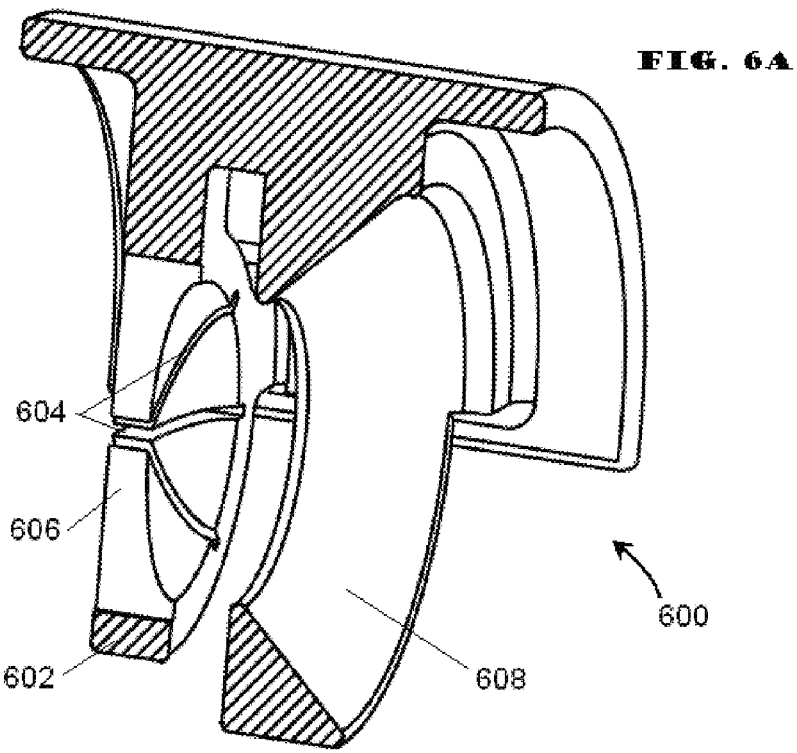
FIG. 6 shows schematic illustrations of details of various forms of diverters which may be utilized in the RSR device according to various embodiments of the present invention.
Figures 6B, 6C:
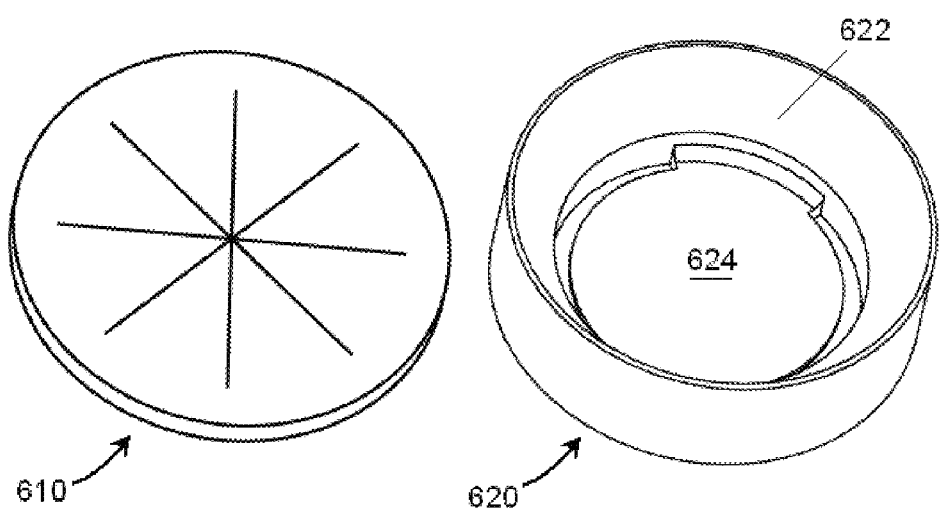

FIGS. 6A, 6B and 6C show schematic illustrations of various additional designs for diverters which allow for the passage of a suction catheter through the diverter portion of RSR devices according to certain configurations if this invention. FIG. 6A shows a cross-sectional illustration of a two-stage diverter. A first stage 602 of the diverter 600 is on the artificial airway port side of the diverter. Multiple slits 604 are shown perforating the first stage 602 of the diverter shown in the configuration of a star shaped, although various forms may be used within the concept of this invention. The first stage 602 may be thin at the center to decrease resistance and help guide passage of an instrument such as a suction catheter through the first stage. The first stage may use material which is flexible and allow deformation so that wedged shaped areas 606 formed by the perforations can bend out of the way of an instrument being passed through this stage of the diverter. The first stage 602 of the diverter 600 can be replaced with a simple flap 514, as is shown in FIG. 5A.

Diverter 600 has a second stage 608. Second stage 608 may have a larger outer diameter than the first stage 602 to enlarge the area of respiratory gas flow diverted. The second stage 608 of the diverter 600 is on the ventilation source side of a RSR device. Second stage 608 may have a funnel shape which can act as a guide for directing an instrument, such as a suction catheter, through the diverter.

FIG. 6B shows a diverter 610 with a star-shaped perforation. Other shapes, sizes and patterns of perforations could be utilized in different embodiments. FIG. 6C illustrates a diverter 620 with a funnel shaped outer ring 622, and a hinged flap valve 624. This diverter outer ring can have a sloped wall 622, which can help guide an instrument. These illustrations are not meant to in any way limit the type of diverter, which may be used to divert secretions or which can be used to allow an instrument to pass through this area of the RSR device, but rather to show some of the possible configurations. A diverter may have one or more stages and the stages may be of similar or different designs.

FIGS. 7A, 7B, 8A and 8B are schematic illustrations constructed in accordance with a further embodiment of the present invention showing an RSR device which allows conformational changes of the device.

FIG. 7A shows a perspective view of a configuration of another embodiment of the invention. RSR device 700 has a connector 710 which allows connection to an artificial airway port and a connector 720 that allows connection to a ventilation source. In a preferred configuration these connectors are standard 15 mm respiratory connectors. In embodiments, connector 710 is a female 15 mm swivel fitting and connector 720 is a male 15 mm fitting which can accept connection to a closed suction device or to a ventilator circuit. RSR device 700 has a ventilation housing 705. Housing 705 has a reservoir portion 750 for collecting secretions. Reservoir 750 can be integral to housing 705 or a separate component. Reservoir 750 may be suctioned through the ventilation housing or may be suctioned through a separate port in the reservoir itself. In embodiments, housing 705 can be flexible by being constructed of a non-rigid material, having thin walls, or by other means known to achieve flexibility. A flexible ventilation housing allows for a conformational change in terms of the alignment of the connector 720 with certain other parts of the structure of the RSR device 700. This conformational change may be achieved through methods such as rotation, bending, translation, etc. A bellows area 715 in the ventilation housing 705 is shown as a way to implement a conformational change.

FIG. 7A shows RSR device 700 can include a support structure 725. Support structure 725 can interface with connector 710, connector 720 and/or ventilation housing 705. Support structure 725 can be integral to one of these components, such as connector 710. In embodiments, support structure 725 can contain a track 736 for interacting with key 735 to allow the RSR device 700 to be held in at least two different conformational positions. Key 735 may extend from connector 720 on a support arm 740. Key 735 can move through track 736. In another embodiment, a key feature or its mating detail in the support structure 725 can deflect to allow for movement and placement into different conformational positions. Various techniques such as tracks, snaps, ratchets, detents, etc. are known for maintaining conformational positions. Support structure 725 also can have a cage 730. Cage 730 can protect a reservoir portion 750 of the housing 705 from inadvertent compression, while allowing for compression with finger pressure, for example, when desired by the user to help evacuate the contents of the reservoir 750.

FIG. 7A shows RSR device 700 in a straight position, which would be used when the device is in normal use, and during suctioning of the artificial airway with a closed suction unit, or when introducing an instrument into the artificial airway as shown in a cutaway view in FIG. 7B.

Figure 8A:
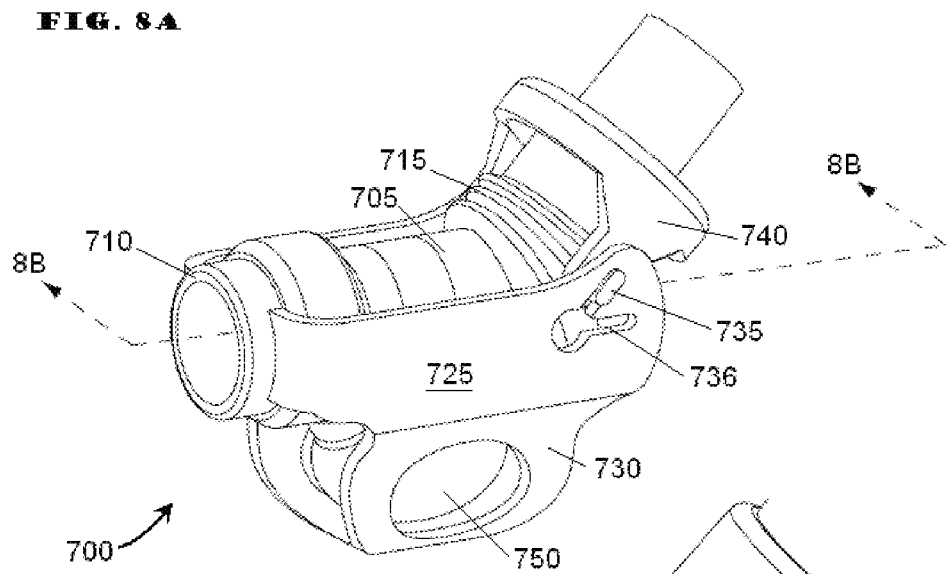
FIG. 8 shows additional schematic illustrations of the RSR device shown in FIG. 7 according to a certain embodiment of the present invention.
Figure 8B:
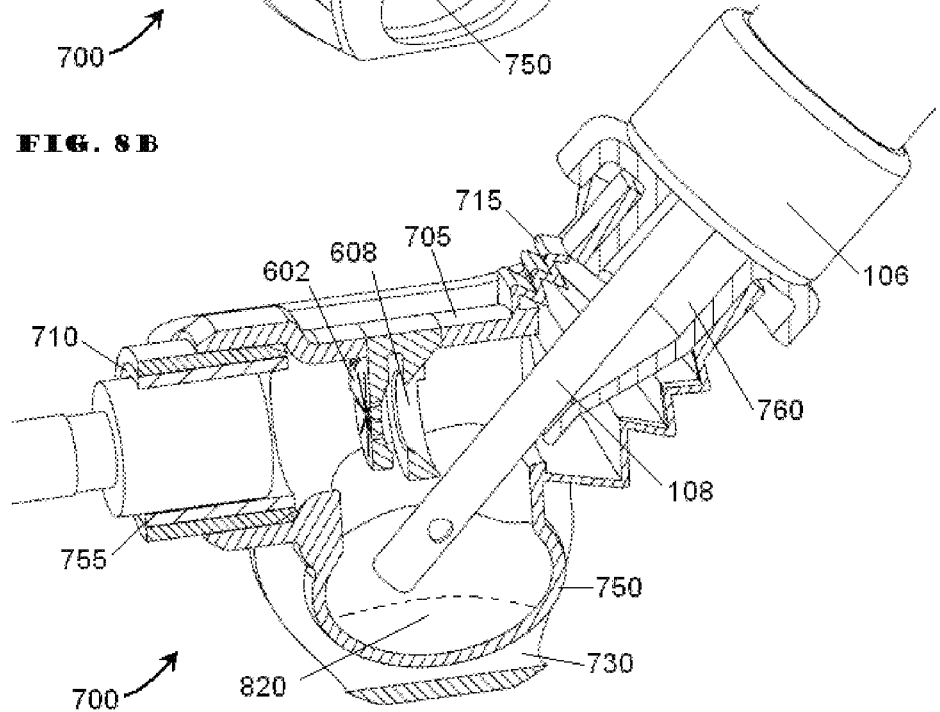

FIG. 8A shows device 700 in a secondary position. In the secondary position, the control key 735 is in a secondary position and the bellows area 715 section of ventilation housing 705 is in a flexed position. This secondary position allows a suction catheter to be inserted into the reservoir area 750 for evacuation of the pooled secretions as shown in FIG. 8B. The reservoir area 750 may be made of a flexible material and may be squeezed by the operator during suctioning to help remove collected respiratory secretions.

FIG. 7B shows a cutaway view of RSR device 700. The catheter 108 can be seen supported by instrument guide 760, and passing through the second stage 608 of diverter 600, which also acts as an instrument guide due to its funnel like shape. The catheter then passes through the first stage 602 of the diverter 600 which acts as a valve, diverting respiratory secretions when closed but allowing passage of the instrument.

FIGS. 8A and 8B show the position for the RSR device in a secondary conformational position for use during suctioning of the reservoir.

FIG. 8B illustrates the RSR device 700 in a cross-sectional view in a secondary conformational alignment which may be used to remove respiratory secretions 820 from reservoir 750 using an instrument such as closed suction catheter 108. Catheter guide 760 can help guide a flexible instrument.

Figure 9:
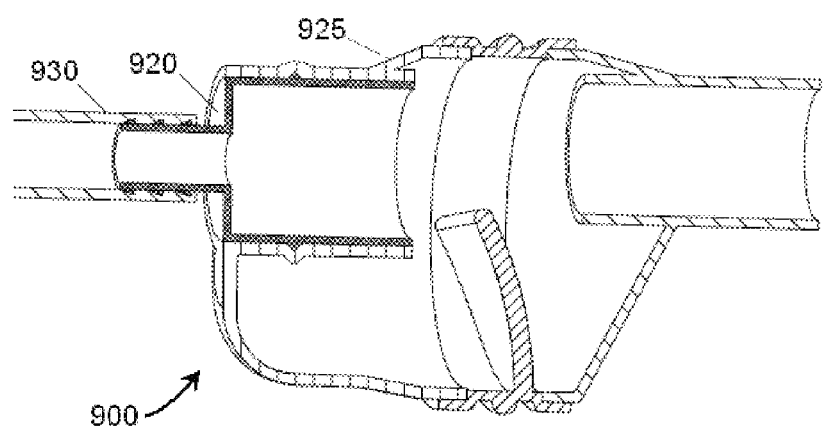
FIG. 9 shows cross-sectional schematic illustrations of variations of the RSR device shown according to a certain embodiment of the present invention.

FIG. 9 is a cross-sectional schematic illustration in accordance with a certain embodiment of the present invention configured with a connecter 920 shown as a Christmas tree or male barbed connector, for connection directly to an endotracheal tube 930. The connector 920 may also connect to the endotracheal tube without the barbs. This configuration replaces the fitting commonly used as the attachment to artificial airway as shown herein in other illustrations, for example the male fitting of artificial airway 102 and port 302 as illustrated in FIG. 3A. A connector such as shown in FIG. 9 allows the RSR device to be integrated as a single unit with the patient artificial airway. FIG. 9 also illustrates that connector 920 can act as a swivel within housing section 925 which allows the device to be rotated in relation to the endotracheal tube. This allows for positioning of the reservoir area of the RSR in a dependent orientation, and also decreases the strain and traction of the artificial airway upon the patient.

In other embodiments, the RSR device 900 can be directly attached to a tracheotomy tube, as RSR device 900 functions to replace the adapter that is standard with ET and tracheotomy tubes. In embodiments, RSR device 900 can be packaged and sterilized with the artificial airways.

Figure 10A:
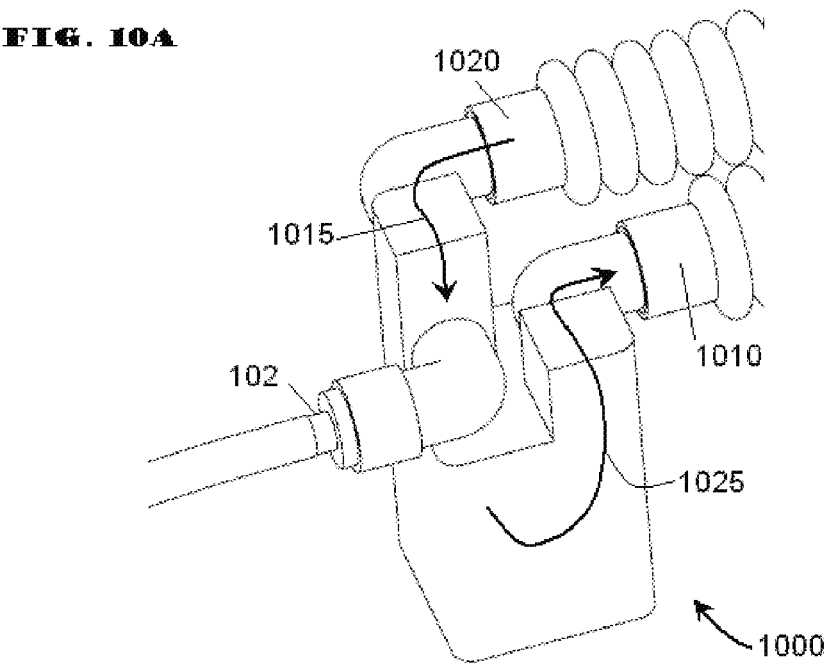
FIG. 10 shows cross-sectional schematic illustrations of variations of the RSR device shown according to a certain embodiment of the present invention.
Figure 10B:
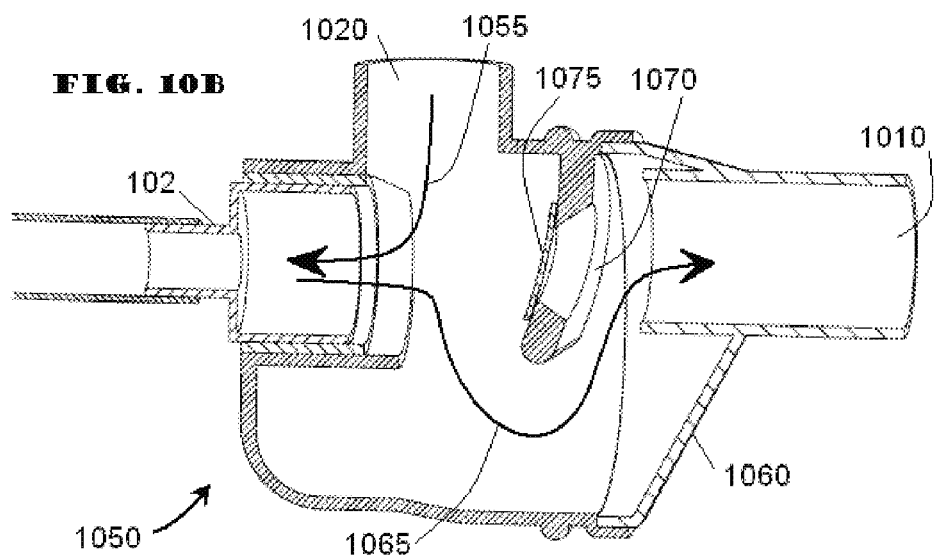

FIGS. 10A and 10B are yet other schematic illustrations of RSR device embodiments according to the present disclosure where the respiratory inflow tract enters at the patient end of the RSR device, and the exhaled gasses pass through the RSR device. This has the added advantage of greatly reducing the volume of dead air space while still providing a larger reservoir. This inspiratory bypass that allows a larger reservoir area, and can be used alone or in combination with valves to prevent efflux of respiratory secretions back into the airway. FIG. 10A illustrates an RSR device 1000 similar to device 200 shown in FIG. 2A. FIG. 10B illustrates an RSR device 1060 similar to RSR device 500. In FIG. 10A, the gas supply enters through delivery port 1020 close to the artificial airway. In device 200, the gas flow is bi-directional and reverses direction during the respiratory cycle. In contrast, in device 1000 flow though the RSR body passes in one direction; away from the patient. Arrow 1015 illustrated the direction of delivery of respiratory gas to the subject from the delivery arm of the ventilator circuit 4420. During expiration breath passes through the RSR device 1000 as shown by arrow 1025 and into the exhalation arm of the ventilator circuit 1010.

In FIG. 10B, the gas supply enters the RSR device through delivery port 1020 and flows to the subject near to the artificial airway 102 as shown by arrow 1055. In similar device 500, the gas flow is bi-directional and reverses direction during the respiratory cycle. In contrast, in RSR device 1050, flow thought the RSR body passes in one direction; away from the patient, as shown by arrow 1065, and flows towards expiratory port 1010.

Another advantage to having a gas inflow tract on the patient side is that if the reservoir side is opened for suctioning, negative pressure is unlikely to occur, and there is less likelihood of patient contamination from the environment. Alternative to having a patient end inflow port configured integral into the RSR, a Tee can be added on the patient end which is placed between the artificial airway and the RSR device. A disadvantage of this that the suction catheter must be extended further to suction the artificial airway.

Figure 11A:
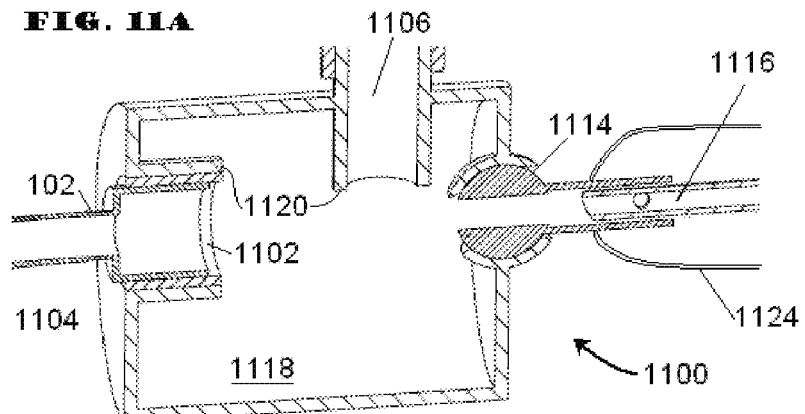
FIG. 11 shows cross-sectional schematic illustrations of variations of the RSR device shown according to a certain embodiment of the present invention.
Figure 11B:
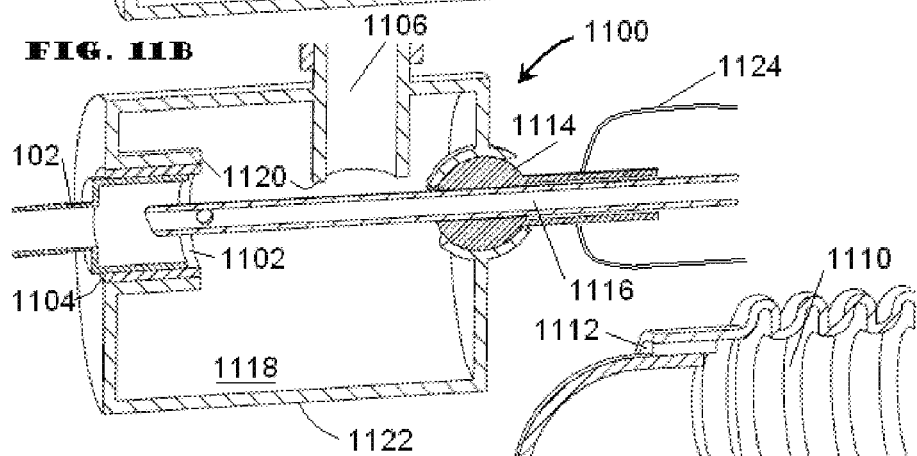
Figure 11C:
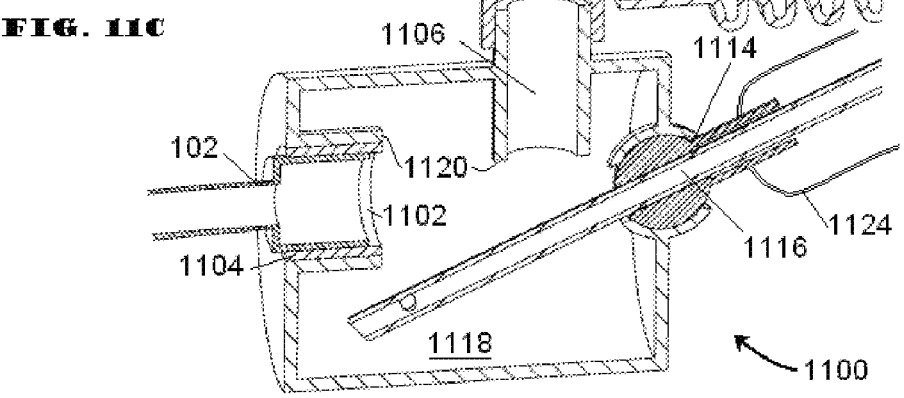

FIGS. 11A and 12A illustrate additional embodiments of the current invention, wherein closed suction allows clearance of respiratory secretions from the artificial airway and from the RSR device. FIG. 11A shows a RSR device 1100 with an integrated closed suction catheter. In RSR device 1100, a suction catheter 1116 can be connected by a fitting 1114. Fitting 1114 allows the suction catheter 1116 to be advanced and withdrawn into and through the body 1122 of RSR device 1100. Fitting 1114 also can pivot to allow the catheter 1116 to enter into the artificial airway for suctioning as shown in FIG. 11B or to enter the reservoir area 1118 for evacuation of accumulated respiratory secretions from the RSR device as illustrated in FIG. 11C. Catheter 1116 is sealed within a protective sheath 1124, which is only partially visible in FIGS. 11A, 11B and 11C. Sheath 1124 is flexible and allows the catheter to be advanced into and retracted from the housing of the RSR device, and prevents contamination of the catheter from the external environment.

FIG. 12A illustrates yet another embodiment of the invention showing an RSR device with an integrated fitting for a closed suction connection. Device 1200 is configured to attach to artificial airway 102 with connector port 1202. A swivel connector, such as 1204 allows a connection, which places less stress on the artificial airway. Stress on the artificial airway may be injurious to the patient, may cause damage to the trachea, and may induce leaking of seal of the balloon of the endotracheal balloon. This may allow upper airway secretions to enter the lung, which is considered to be a risk factor for ventilator associated pneumonia.

FIGS. 12A and 12B show a gas flow path diverter 1206. Diverter 1206 contains a valve 1208 and bevels 1210 which act an instrument guide. A suction catheter 108 is illustrated in FIG. 12B through the diverter. The diverter 1206 is shown as being supported by support arms 1212. In other configurations, the diverter could be attached to an interior wall, a swivel connector, or to the ventilation source side of the RSR device.

FIGS. 12B and 12C show device 1200 illustrated with a fitting 1214 to allow for connection to a closed suction device 106. The fitting 1214 is designed to allow flow of gas. Fitting 1214 can pivot to allow the catheter 108 to enter into the artificial airway for suctioning as shown in FIG. 12B or to enter the reservoir area 1216 for evacuation of accumulated respiratory secretions from the RSR device 1200 as illustrated in FIG. 12C. The catheter 108 would be withdrawn into the closed suctioning device during its typical use.

Figure 13A:
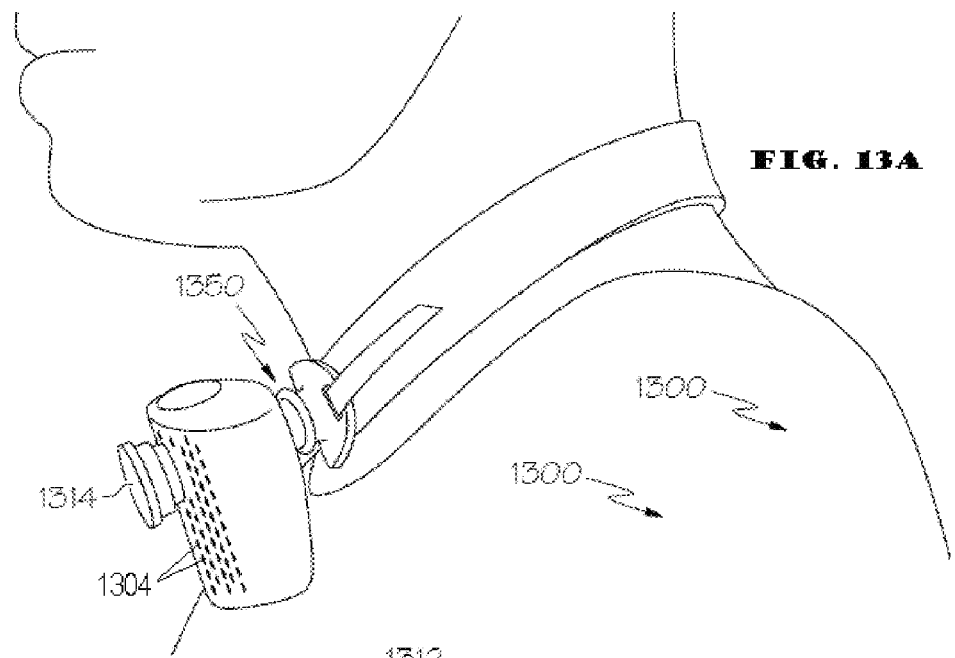
FIG. 13A shows lateral schematic view of a configuration of an RSR device shown according to a certain embodiment of the present invention.
Figure 13B:
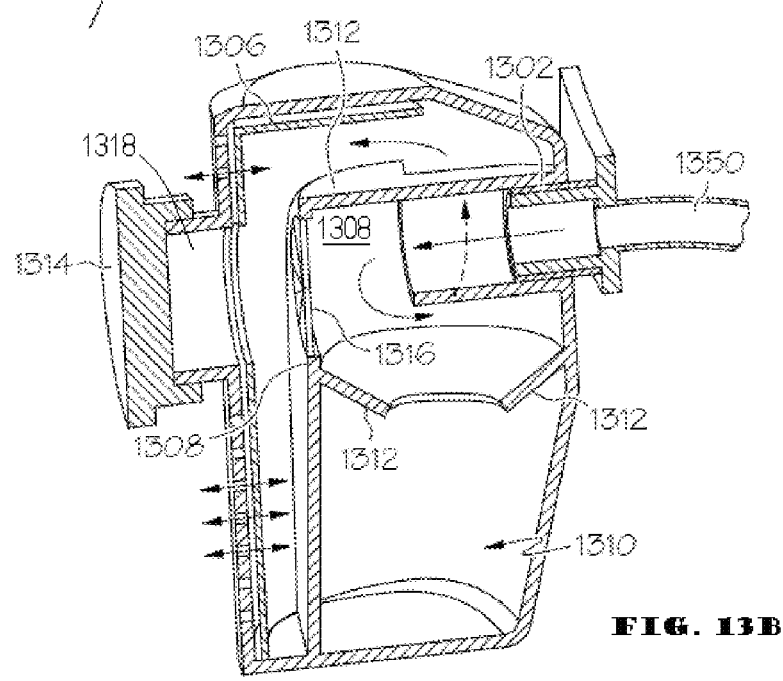
FIG. 13B shows a frontal schematic view of the RSR device shown in FIG. 13A.

FIG. 13 illustrates yet another embodiment of an RSR device according to the present invention. RSR device 1300 is configured to fit to a tracheostomy tube 1350. A connector 1302, e.g., a swivel connector, is shown in FIG. 13A which allows orientation of the reservoir area 1320 in a dependent position for collection of respiratory secretions. In contrast to having a single gas flow vent (e.g., exhalation port) configured to couple with another device, device 1300 is an example of a configuration of an RSR device with multiple perforations or vents 1304 for direct flow to and from the device to the atmosphere. Vents are illustrated on the anterior surface, but can be on other surfaces. The anterior and upper portion is shown containing heat and moisture exchange (HME) material 1306 which acts as a filter helping to protect the patient's airway from airborne pathogens. The HME material also acts to capture heat and humidity from the patient's exhaled breath, and release it back to the patient upon inhalation, thus avoiding drying of the airways and avoiding energy loss from the patient. FIG. 13B shows that within device 1300 an airflow diverter wall 1308 which helps capture respiratory secretions and guide them towards the reservoir area 1310 and towards the lower internal surface of the housing. Diverter wall 1308 helps to separate respiratory secretions from the gas flow. RSR device 1300 also has spill guards 1312 which help retain secretions in the reservoir area and help prevent spillage of retained respiratory secretions in the event that the patient's position is moved.

The exhaled breath flows first towards the deflector and then flows through the HME material 1306 where heat and moisture is captured and the remaining exhaled gas can pass to the atmosphere through vents 1304. On inspiration, atmospheric gas enters through vents 1304 is filtered, heated and humidified before flowing into the patient airway.

The device in FIG. 13B shows an orifice 1318 with a cap 1314 on the front surface of device 1300 which may be opened if suctioning is desired. Deflector wall 1308 is illustrated in FIG. 13B with a valve 1316 that allows a suction catheter or other instrument to be introduced into the artificial airway 1350 with access being given by opening cap 1314. In certain embodiments, RSR device 1300 may be configured so that a suction catheter may be directed to enter reservoir area 1310. This allows for removal of respiratory secretions from the device. In other configurations, the RSR device 1300 can be configured without these features.

Not shown in the illustration, the cap may cover a second valve at the surface of the RSR device 1300. Such a valve would help prevent sputum from entering the room during suctioning, and limit inhalation of unfiltered air. Valve 1316 can have, for example a conformation similar to valve 610 shown in FIG. 6B. In another embodiment, the device can be made with a valve without a cap. In a configuration of the invention, one or more valves can be configured as an anti-asphyxiation valve which would open in the case that the resistance to flow through HME material and surface vents became higher than desirable.

Device 1300 may be preferentially constructed with a housing made of a flexible material, such as silicone, to make wearing the device more comfortable for the patient. The device may also be configured so that it may be cleansed and the HME material or HME section may be replaced.

FIG. 14 illustrates another embodiment of an RSR device 1400 according to the present invention. Housing 1405 has a patient port 1420 for connection to an artificial airway and a ventilation port 1430 for connection to a closed suction device and/or ventilation source (not shown). The ports can have swivel connectors to facilitate orientation of the RSR device. Housing 1405 also has a reservoir 1450 for collection of respiratory secretions. Opening 1490 allows secretions to enter the reservoir as they pass through the housing. The opening may be sized large enough to maximize the entry of the secretions. Features such as a diverter, which were described in other embodiments of this invention, can also be located in RSR device 1400 to further separate secretions from the gas flow and direct them into the reservoir. The RSR device 1400 may be disposed of with the contained secretions, or the secretions may be removed by a variation of methods such as removing the reservoir, draining the reservoir, or suctioning the reservoir and/or housing, etc. In embodiments, the reservoir may be flexible. A flexible reservoir may be collapsed, for example by squeezing, or translated into the housing in order to move the secretions into main section of the housing. Once the secretions are moved there, the secretions may be removed, for example by a suction catheter 1410.

FIG. 15A illustrates a RSR device 1500 similar to RSR device 1400. Housing 1505 can include a diverter 1520 as shown. Housing 1505 further can include a flexible portion 1570 with a guide 1580. The flexible portion 1570 can provide the guide to translate with respect to the interior of the housing. In FIG. 15B, a suction catheter 1510 is shown passing through the housing in order to suction an artificial airway of a patient. In FIG. 15C, the guide is shown translated further into the housing and therefore directing the suction catheter into a reservoir 1550 in order to remove secretions.

FIG. 16A illustrates a RSR device 1600 similar to RSR device 1400. Housing 1605 has a diverter 1620 as shown. Housing 1605 has a guide 1680 that can direct an instrument, such as a suction catheter, towards the diverter or towards a reservoir 1650. Guide 1680 can be integral to housing 1605 or it could be a separate piece. If a separate piece, guide 1680 may pivot within housing 1605 allowing for increased directional control of a suction catheter. A pivoting guide may extend through the housing in a sealed manner to allow a user to externally control the angle of the guide. An external knob or similar detail could be attached to the extended part of the guide to allow the user to pivot the guide. In FIG. 16B, a suction catheter 1610 is shown passing above the guide in the housing in order to suction an artificial airway of a patient. In FIG. 16C, a suction catheter 1610 is shown passing below the guide directing the suction catheter into a reservoir 1650 in order to remove secretions.

Figure 17A:
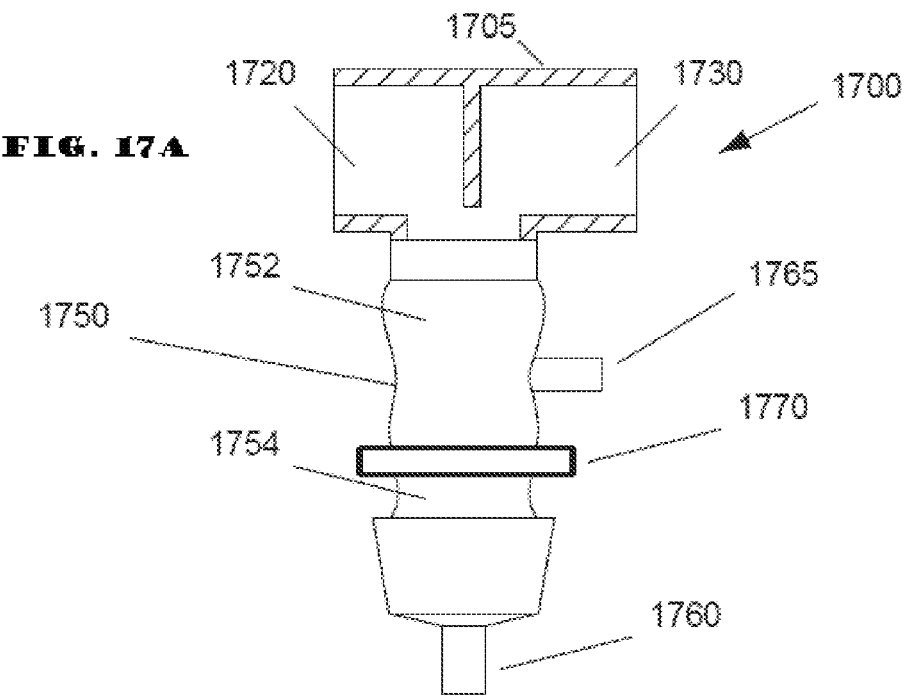
Figure 17B:
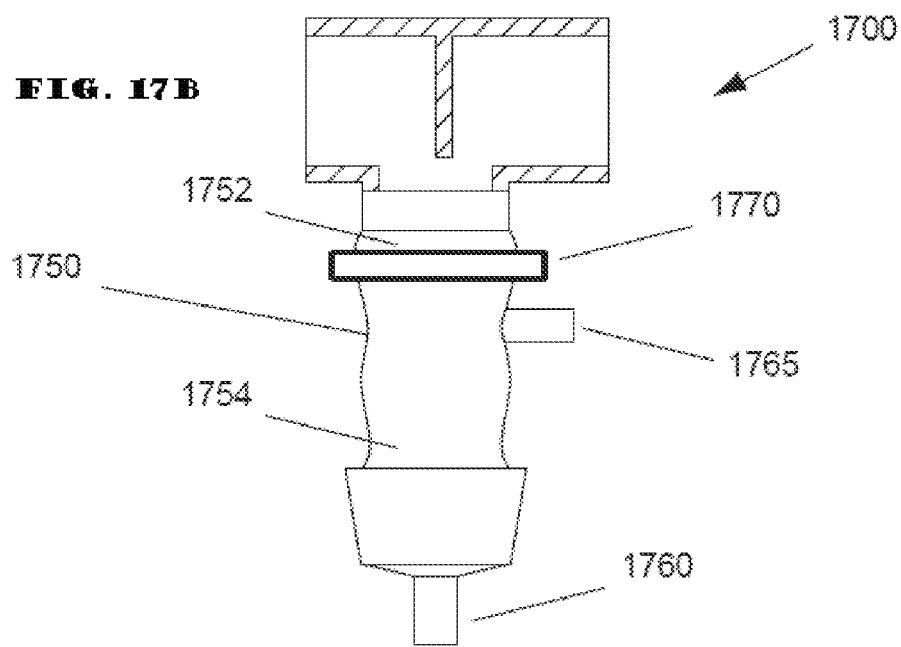

FIGS. 17A and 17B illustrate another embodiment of and RSR device 1700 according to the present invention. Housing 1705 has a patient port 1720 for connection to an artificial airway and a ventilation port 1730 for connection to a closed suction device and/or ventilation source (not shown). The ports may have swivels to facilitate orientation of the RSR device. Housing 1705 also has a reservoir 1750 for collection of respiratory secretions. The reservoir 1750 may be flexible or have a flexible extension, which allows the size of the reservoir to be controlled. Features such as a diverter, which were described in other embodiments of this invention, may also be located in the RSR device 1700 to further separate secretions from the gas flow and direct them into the reservoir 1750. A drain or vacuum port 1760 may be included which allows for emptying the contents of the reservoir. In one embodiment, a RSR device 1700 can include a drain port 1760 and a fluid instillation port 1765. Instillation port 1765 can be used to instill saline or other fluid to help clear the respiratory secretions which have collected in the reservoir, especially if these secretions are thick or tenacious.

A clip 1770 can be applied to the reservoir 1750 to divide the volume of the reservoir to an upper area 1752 above the clip 1770 and a lower area 1754 below the clip 1770. A smaller reservoir volume is advantageous to limit dead space volume, especially for example in smaller patients and in patients with certain respiratory diseases. A larger reservoir volume is advantageous to allow for less frequent clearing of the secretions in the RSR device 1700. The position of the clip 1770 may be adjustable on the reservoir and therefore limiting the volume in the upper area 1752 as desired by the user.

As shown in FIG. 17B, clip 1770 could be removed and then attached above the fluid instillation port 1765, allowing the reservoir to be cleared while maintaining a minimum deadspace in the upper area 1752, maintaining a closed air circuit, and preventing the patient from experiencing the effects of the clearing, such as with a vacuum. When the reservoir 1750 begins to fill with respiratory secretions during use, the clip position may be adjusted to enlarge the upper area 1752. The clip 1770 also can be removed to allow the secretions to pool in the lower area 1754 of the reservoir, and then the clip may be reattached to again limit the reservoir volume. The clip 1770 could then also be used as a tool to force the secretions lower into the lower area 1754 of the reservoir. The secretions now in the lower area 1754 of the reservoir may be drained through a port 1760 or may be maintained there until the device or reservoir is disposed.

Several other possible configurations of this invention can easily come to mind by those skilled in the art, which are within the scope of this invention. For example, the route for passage of a suction catheter in most configurations may as well be used for passage of a stylette for use in facilitating intubation, for passage of a bronchoscope or the like. The connection port for the artificial airway for RSR devices can have a 15 mm inner diameter (ID); however, it could be any ID necessary to connect with various artificial airway tubes or the like. The connection port of the ventilation source can have 15 mm outer diameter; however, it could be any ID necessary to connect with a ventilator circuit, closed suction device, or similar device, or may be used open to the atmosphere.

In addition, although not required for function of this invention, the use of clear materials is desirable as it aids in determining the amount of fluid sequestered in the RSR device. In addition, the RSR device can be made of or coated with antimicrobial substances or materials to prevent the growth of bacteria, and other microbes, for example antimicrobial substances that prevent the formation of biofilms on or within the RSR device. Further coatings or materials with hydrophilic properties may be used to improve the retention of secretions in a reservoir area. Further coatings or materials with hydrophobic properties may be used to decrease adhesion of secretions to the diverter or other surfaces in the RSR device. A hydrophobic diverter is more likely to shed tenacious secretions off the diverter and into the reservoir during high flow ventilation.

While the invention has been described in terms of what is presently considered to be the most practical and preferred embodiments, it is to be understood that the invention needs not be limited to the disclosed embodiment. On the contrary, it is intended to cover various modifications and similar arrangements included within the spirit and scope of the appended claims, which are to be accorded with the broadest interpretation so as to encompass all such modifications and similar structures.

We claim:

1. A respiratory secretion retention device configured for fluidly connecting to an artificial airway, the device comprising:
   an artificial airway side port;
   an inlet configured to allow respiratory gas to flow towards the artificial airway side port;
   a housing, the housing defining a passageway for the flow of respiratory gases;
   a chamber defined by the housing, a portion of the chamber configured to retain exhaled respiratory particulate and liquid, wherein the chamber is closed from atmosphere; and,
   at least a portion of the housing configured to reposition with respect to the artificial airway side port.

2. The device of claim 1, wherein the at least a portion of the housing can be repositioned with respect to the artificial airway without opening the artificial airway to atmosphere.

3. The device of claim 1, wherein the device is configured to reposition at least a portion of the housing in only two positions with respect to the artificial airway side port.

4. The device of claim 1, wherein the device is configured to reposition at least a portion of the housing in at least two positions with respect to the artificial airway.

5. The device of claim 1, wherein the device is configured to allow a medical instrument to pass through the housing and into the artificial airway.

6. The device of claim 1, wherein the device is configured to allow a medical instrument to pass to at least one area within the housing to remove retained fluids within the housing.

7. The device of claim 1, wherein an instrument guide is positioned within the inlet and configured to route a medical instrument to one of an artificial airway and a chamber.

8. The device of claim 7, wherein the position of the instrument guide is adjustable.

9. The device of claim 1, wherein at least one portion of an interior surface of device includes a property selected from the group consisting of a hydrophilic property, a hydrophobic property and an antimicrobial property.

10. The device of claim 1, wherein the device includes one component selected from the group consisting of an artificial airway, a closed suction device, a heat and moisture exchange device, a fitting, tubing and a respiratory gas device.

11. A respiratory secretion retention device configured for fluidly connecting to an artificial airway, the device comprising:
 a housing, the housing defining a passageway for the flow of respiratory gases;
 a chamber defined by the housing, a portion of the chamber configured to retain exhaled respiratory particulate and liquids, wherein the chamber is closed from atmosphere; and,
 a medical instrument port coupled within the housing, the medical instrument port configured to allow a medical instrument to advance into the chamber without opening the respiratory secretion retention device to the atmosphere.

12. The device of claim 11, wherein at least a section of the chamber is configured to provide for repositioning of the chamber to allow for the removal of the retained secretions from within the device.

13. A respiratory secretion retention device configured for fluidly connecting to an artificial airway, the device comprising:
 a housing, the housing defining a passageway for the flow of respiratory gases;
 a chamber defined by the housing, a portion of the chamber configured to retain exhaled respiratory particulate and liquids, wherein the chamber is closed from atmosphere; and,
 a medical instrument port coupled within the housing, the medical instrument port configured to allow a medical instrument to advance through the housing from the medical instrument port to a port on the artificial airway side without opening the respiratory secretion retention device to the atmosphere.

14. The device of claim 13, wherein at least a portion of the housing is configured to provide for repositioning of the housing to allow for the removal of the retained secretions from within the device.

15. The device of claim 13, wherein the medical instrument port is configured to provide for repositioning of the medical instrument to allow for the removal of the retained secretions from within the device.

16. The device of claim 13, further comprising a gas port coupled within the housing.

17. The device of claim 13, wherein the respiratory secretion retention device further comprises a medical instrument integrated with the respiratory secretion retention device.

18. A respiratory secretion retention device configured for fluidly connecting to an artificial airway, the device comprising:
 a housing, the housing defining a passageway for the flow of respiratory gases;
 a chamber defined by the housing, a portion of the chamber configured to retain exhaled respiratory particulate and liquid; and,
 at least one diverter positioned within the flow passageway and positioned internal within the housing, wherein the at least one diverter includes an aperture, the aperture defining an instrument passage.

19. The device in claim 18, wherein the aperture includes a valve, the valve being configured to at least partially obstruct the aperture in the at least one diverter when the instrument passage is not in use.

20. The device in claim 18 wherein the at least one diverter is configured to assist in guiding the passage of a medical instrument.

21. The device of claim 18, wherein a first portion of the housing can be repositioned with respect to a second portion of the housing so that the at least one diverter is absent from the flow passageway.

22. The device of claim 18, wherein at least one portion of an interior surface of the device includes a property selected from the group consisting of a hydrophilic property, a hydrophobic property and an antimicrobial property.

23. The device of claim 18, wherein the device includes a component selected from the group consisting of an artificial airway, a closed suction device, a heat and moisture exchange device, a fitting, tubing and a respiratory gas device.

24. The device of claim 18, wherein an instrument guide is positioned within the housing and configured to route a medical instrument to one of an artificial airway and a chamber.

25. The device of claim 24, wherein the position of the instrument guide is adjustable.

* * * * *